United States Patent
Brannan et al.

(10) Patent No.: US 11,931,139 B2
(45) Date of Patent: Mar. 19, 2024

(54) SYSTEM AND METHOD FOR LUNG VISUALIZATION USING ULTRASOUND

(71) Applicant: COVIDIEN LP, Mansfield, MA (US)

(72) Inventors: Joseph D. Brannan, Lyons, CO (US); William J. Dickhans, Longmont, CO (US); Casey M. Ladtkow, Erie, CO (US); Darion R. Peterson, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1171 days.

(21) Appl. No.: 16/160,390

(22) Filed: Oct. 15, 2018

(65) Prior Publication Data

US 2019/0046071 A1 Feb. 14, 2019

Related U.S. Application Data

(63) Continuation of application No. 14/469,728, filed on Aug. 27, 2014, now Pat. No. 10,098,566.
(Continued)

(51) Int. Cl.
*A61B 5/06* (2006.01)
*A61B 1/267* (2006.01)
(Continued)

(52) U.S. Cl.
CPC .............. *A61B 5/062* (2013.01); *A61B 1/267* (2013.01); *A61B 5/113* (2013.01); *A61B 5/7207* (2013.01);
(Continued)

(58) Field of Classification Search
CPC ......... A61B 5/062; A61B 1/267; A61B 5/113; A61B 5/7207; A61B 8/12; A61B 8/4254;
(Continued)

(56) References Cited

U.S. PATENT DOCUMENTS

| 5,244,462 A | 9/1993 | Delahuerga et al. |
| 5,531,520 A | 7/1996 | Grimson et al. |

(Continued)

FOREIGN PATENT DOCUMENTS

| CN | 1628602 A | 6/2005 |
| CN | 1853574 A | 11/2006 |

(Continued)

OTHER PUBLICATIONS

Fusaroli et al., "Forward-view Endoscopic Ultrasound: A Systematic Review of Diagnostic and Therapeutic Applications," (Apr. 2, 2013) Endosc Ultrasound 2013; 2(2): 64-70. (Year: 2013).*

(Continued)

*Primary Examiner* — Joel Lamprecht
*Assistant Examiner* — Ashish S Jasani
(74) *Attorney, Agent, or Firm* — Weber Rosselli & Cannon LLP

(57) ABSTRACT

A system for ultrasound interrogation of a lung including a memory, an electromagnetic (EM) board, an extended working channel (EWC), an EM sensor, a US transducer, and a processor. The memory stores a three dimensional (3D) model and pathway plan for navigating a luminal network. The EM board generates an EM field. The EWC is configured to navigate the luminal network toward a target following the pathway plan. The EM sensor extends distally from a distal end of the EWC and is configured to sense the EM field. The US transducer extends distally from a distal end of the EWC, generates US waves, and receives US waves reflected from the luminal network. The processor processes the sensed EM field to synchronize a location of the EM sensor in the 3D model, to process the reflected US waves to generate images, or to integrate the generated images with the 3D model.

20 Claims, 7 Drawing Sheets

Related U.S. Application Data

(60) Provisional application No. 62/041,850, filed on Aug. 26, 2014, provisional application No. 62/041,842, filed on Aug. 26, 2014, provisional application No. 61/874,881, filed on Sep. 6, 2013.

(51) Int. Cl.
*A61B 5/00* (2006.01)
*A61B 5/113* (2006.01)
*A61B 8/00* (2006.01)
*A61B 8/08* (2006.01)
*A61B 8/12* (2006.01)

(52) U.S. Cl.
CPC .............. *A61B 8/12* (2013.01); *A61B 8/4254* (2013.01); *A61B 8/5238* (2013.01); *A61B 8/08* (2013.01); *A61B 8/463* (2013.01); *A61B 8/467* (2013.01); *A61B 8/5261* (2013.01)

(58) Field of Classification Search
CPC ......... A61B 8/5238; A61B 8/08; A61B 8/463; A61B 8/467; A61B 8/5261; A61B 5/66; A61B 5/267; A61B 5/005; A61B 5/06; A61B 5/064
See application file for complete search history.

(56) References Cited

U.S. PATENT DOCUMENTS

| | | | |
|---|---|---|---|
| 5,569,289 A | 10/1996 | Yoon | |
| 5,633,951 A | 5/1997 | Moshfeghi | |
| 6,019,724 A | 2/2000 | Gronningsaeter et al. | |
| 6,749,606 B2 | 6/2004 | Keast et al. | |
| 7,835,785 B2 | 11/2010 | Scully et al. | |
| 7,883,471 B2 | 2/2011 | Aljuri et al. | |
| 7,889,905 B2 | 2/2011 | Higgins et al. | |
| 7,901,348 B2 | 3/2011 | Soper et al. | |
| 7,985,187 B2 | 7/2011 | Wibowo et al. | |
| 8,357,193 B2 | 1/2013 | Phan et al. | |
| 8,382,662 B2 | 2/2013 | Soper et al. | |
| 8,454,527 B2 | 6/2013 | Aljuri et al. | |
| 8,821,376 B2 | 9/2014 | Tolkowsky | |
| 2003/0013958 A1 | 1/2003 | Govari et al. | |
| 2005/0107688 A1 | 5/2005 | Strommer | |
| 2005/0182295 A1 | 8/2005 | Soper et al. | |
| 2005/0283067 A1 | 12/2005 | Sobe | |
| 2006/0149134 A1 | 7/2006 | Soper | |
| 2006/0173319 A1* | 8/2006 | Sumi ................... G01S 7/52095 | 600/437 |
| 2006/0253031 A1 | 11/2006 | Altmann et al. | |
| 2007/0027392 A1 | 2/2007 | Schwartz | |
| 2007/0055128 A1* | 3/2007 | Glossop ................. A61B 1/018 | 600/407 |
| 2007/0078334 A1 | 4/2007 | Scully et al. | |
| 2008/0071140 A1 | 3/2008 | Gattani | |
| 2008/0118135 A1 | 5/2008 | Averbuch et al. | |
| 2008/0119727 A1* | 5/2008 | Barbagli ................. A61B 8/12 | 600/437 |
| 2008/0207997 A1 | 8/2008 | Higgins et al. | |
| 2008/0221409 A1 | 9/2008 | Hoarau | |
| 2008/0287803 A1 | 11/2008 | Li et al. | |
| 2009/0105579 A1 | 4/2009 | Garibaldi | |
| 2009/0118727 A1 | 5/2009 | Pearson et al. | |
| 2009/0299352 A1 | 12/2009 | Zerfas et al. | |
| 2010/0041949 A1* | 2/2010 | Tolkowsky ...... A61B 17/12104 | 600/117 |
| 2010/0145186 A1 | 6/2010 | McGrath et al. | |
| 2010/0280363 A1 | 11/2010 | Skarda et al. | |
| 2010/0317964 A1 | 12/2010 | Hendriks et al. | |
| 2011/0060185 A1* | 3/2011 | Ikuma .................. A61B 5/7214 | 600/114 |
| 2011/0184238 A1 | 7/2011 | Higgins et al. | |
| 2011/0230758 A1* | 9/2011 | Eichler ................... A61B 5/6852 | 600/424 |
| 2011/0301438 A1 | 12/2011 | Sachse et al. | |
| 2012/0004537 A1* | 1/2012 | Tolkowsky .............. A61B 8/12 | 600/424 |
| 2012/0046521 A1* | 2/2012 | Hunter ................. A61B 8/0841 | 600/104 |
| 2012/0059248 A1 | 3/2012 | Holsing et al. | |
| 2012/0071749 A1* | 3/2012 | Xu ........................... A61B 8/12 | 600/407 |
| 2012/0155731 A1* | 6/2012 | Weersink ................ G06T 7/344 | 382/128 |
| 2012/0197145 A1 | 8/2012 | Wu | |
| 2012/0203067 A1* | 8/2012 | Higgins ................ A61B 34/20 | 600/117 |
| 2012/0209106 A1* | 8/2012 | Liang ..................... A61B 34/20 | 600/414 |
| 2012/0238806 A1 | 9/2012 | Mangiardi et al. | |
| 2012/0289772 A1 | 11/2012 | O'Connell et al. | |
| 2013/0023729 A1 | 1/2013 | Vazales et al. | |
| 2013/0060240 A1 | 3/2013 | Scheller et al. | |
| 2013/0217947 A1* | 8/2013 | Fishman ................ A61B 8/483 | 600/1 |
| 2013/0231557 A1 | 9/2013 | Li | |
| 2013/0317363 A1* | 11/2013 | Case ...................... A61B 8/483 | 600/439 |
| 2014/0105472 A1 | 4/2014 | Yin et al. | |

FOREIGN PATENT DOCUMENTS

| | | | |
|---|---|---|---|
| CN | 101862205 A | 10/2010 | |
| CN | 102319117 A | 1/2012 | |
| CN | 102883651 A | 1/2013 | |
| CN | 102970945 A | 3/2013 | |
| CN | 103025262 A | 4/2013 | |
| CN | 103027712 A | 4/2013 | |
| CN | 105636519 A | 6/2016 | |
| EP | 1929956 A2 | 6/2008 | |
| EP | 2238901 A2 | 10/2010 | |
| JP | 2004097537 A | 4/2004 | |
| JP | 2005522274 A | 7/2005 | |
| JP | 2006305361 A | 11/2006 | |
| JP | 2008512171 A | 4/2008 | |
| JP | 2009142653 A | 7/2009 | |
| KR | 1020110078271 A | 7/2011 | |
| WO | 0134051 A2 | 5/2001 | |
| WO | WO-2005102175 A2 * | 11/2005 | ........... A61B 1/0005 |
| WO | 2008125910 A2 | 10/2008 | |
| WO | 2011062035 A1 | 5/2011 | |
| WO | 2016033090 A1 | 3/2016 | |

OTHER PUBLICATIONS

Hatt et al., "MRI-3D ultrasound-X-ray image fusion with electromagnetic tracking for transendocardial therapeutic injections: In-vitro validation and in-vivo feasibility," (Mar. 2013), Computerized Medical Imaging and Graphics 37 (2013) 162-173. (Year: 2013).*

Lang et al., "Calibration of 3D ultrasound to an electromagnetic tracking system," (Mar. 25, 2011), Proc. SPIE 7968, Medical Imaging 2011: Ultrasonic Imaging, Tomography, and Therapy, 79680W. (Year: 2011).*

Ewertsen et al., "Real-Time Image Fusion Involving Diagnostic Ultrasound," (Mar. 2013), American Journal of Roentgenology. 2013;200: W249-W255/ (Year: 2013).*

Leong et al., "Electromagnetic navigation bronchoscopy: A descriptive analysis," (Apr. 2012), J Thorac Dis. Apr. 1, 2012; 4(2): 173-185. (Year: 2012).*

Yasufuku et al., "Endobronchial Ultrasonography: Current Status and Future Directions," (Oct. 2007), Journal of Thoracic Oncology • vol. 2, No. 1. (Year: 2007).*

Estepar et al., "Towards real time 2D to 3D registration for ultrasound-guided endoscopic and laparoscopic procedures," (Jun. 18, 2010), Int J Comput Assist Radiol Surg. Nov. 2009 ; 4(6): 549-560. (Year: 2010).*

Winter et al., "Registration of CT and Intraoperative 3-D Ultrasound Images of the Spine Using Evolutionary and Gradient-Based Meth-

(56) References Cited

OTHER PUBLICATIONS ods," (Jun. 2008), 284 IEEE Transactions on Evolutionary Computation, vol. 12, No. 3. (Year: 2008).*
Japanese Office Action dated Oct. 23, 2018 in corresponding Japanese Patent Application No. 2018-011132, with English translation.
Yasufuku, Kazuhiro et al., "Endobronchial Ultrasonography: Current Status and Future Directions," State of the Art: Concise Review, Journal of Thoracic Oncology, Oct. 2007, pp. 970-979, vol. 2, No. 10.
European Examination Report dated Oct. 29, 2018 in corresponding European Patent Application No. 14842294.2.
European Examination Report dated Oct. 29, 2018 in corresponding European Patent Application No. 14842874.1.
Notification of the Second Office Action issued by the State Intellectual Property Office of the People's Republic of China dated Mar. 4, 2019 in corresponding Chinese Patent Application No. 201480056086.8 with English translation.
Notification of the Second Office Action issued by the State Intellectual Property Office of the People's Republic of China dated Mar. 4, 2019 in corresponding Chinese Patent Application No. 201480056083.4 with English summary and brief explanation of grounds of rejection.
Canadian Office Action issued in corresponding Appl. No. CA 2,923,459 dated Jul. 3, 2020 (4 pages).
International Search Report issued in corresponding PCT application No. PCT/US2014/053882 dated Dec. 12, 2014.
International Search Report issued in related PCT application No. PCT/US2014/053878 dated Dec. 15, 2014.
International Search Report issued in corresponding PCT application No. PCT/US2014/053890 dated Nov. 24, 2014.
Supplementary European Search Report issued in corresponding Application No. EP 14 84 2874, dated Apr. 12, 2017.
Luo et al., Beyond Current Guided Bronchoscopy: A robust and real-time bronchoscopic ultrasound navigation system in: Lecture Notes in Computer Science (LNCS): Medical Image Computing and Computer-Assisted Intervention—MICCAI 2013, vol. 8149, pp. 388-395 (2013).
Krimsky et al., Bronchoscopy and the peripheral nodule in the age of lung cancer screening and targeted therapies, Current Respiratory Care Reports, vol. 1, No. 1, Jan. 25, 2012, pp. 67-71.
Herth, Bronchoscopic techniques in diagnosis and staging of lung cancer, Breathe, vol. 7, No. 4, Jun. 1, 2011, pp. 329, 332.
Schwarz, Yehuda, MD, FCCP, "Electromagnetic Navigation", Clinics in Chest Medicine, vol. 31, No. 1, Mar. 1, 2010, pp. 65-73, 10 pages.
Supplementary European Search Report issued in corresponding Application No. EP 14842294, dated Apr. 11, 2017, 12 pages.
Office Action for corresponding Chinese Application No. 201480056085.3 dated Aug. 2, 2017.
Randy Hou et al: "Recent advances in optical coherence tomograpy for the diagnoses of lung disorders". Expert Review of Respiratory Medicine, vol. 5, No. 5, Oct. 1, 2011, pp. 711-724.
Pyng Lee et al: "Bronchoscopy in Lung Cancer—Appraisal of Current Technology and for the Future", Journal of Thoracic Oncology, vol. 5, No. 8, Aug. 1, 2010, pp. 1290-1300.
Bojan Zaric et al: "Diagnostic value of autofluorescence bronchoscopy in lung cancer", Thoracic Cancer, vol. 4, No. 1, Feb. 1, 2013, pp. 1-8.
Supplementary European Search Report issued in corresponding EP Application No. 14842292 dated Apr. 11, 2017, 9 pages.
Supplementary European Search Report for corresponding EP Application No. 14841710.8, dated Apr. 11, 2017, 12 pages.
Office Action for corresponding Japanese Application No. 2016-540341 dated Jun. 20, 2017, 19 pages.
Japan Electronics and Information Technology Industries Association, Kaitei Iyou Choonpa Kiki Handobuku, Japan, Corona, Jan. 20, 1997, p. 15, p. 35. (A part or the whole of the non-patent literature indicated above may not be forwarded due torestrictions arising from law or contract.).
Supplementary European Search Report for corresponding European Application No. 14843010.1 dated Jun. 26, 2017, 13 pages.
Chinese Office Action dated Aug. 18, 2017, issued in CN Application No. 201480057462.5.
Office Action for corresponding Chinese Application No. 201480056082.X dated May 25, 2017.
Chinese Office Action dated Apr. 17, 2018 and issued in corresponding Chinese Patent Application No. 201480056085.3, together with English translation.
Chinese Office Action dated Feb. 11, 2018 and issued in Chinese Patent Application No. 201480056082.X together with English translation.
Japanese Office Action dated Mar. 20, 2018 and issued in corresponding Japanese Patent Application No. 2016-540343 together with English translation.
Australian Examination Report dated May 14, 2018 in corresponding Australian Patent Application No. 2014315356.
Australian Examination Report dated May 9, 2018 in corresponding Australian Patent Application No. 2014315359.
Australian Examination Report dated May 14, 2018 in corresponding Australian Patent Application No. 2014315359.
Chinese Office Action dated Jun. 20, 2018 in corresponding Chinese Patent Application No. 201480056086.8, together with English translation.
Australian Examination Report dated May 21, 2018 in corresponding Australian Patent Application No. 2014317930.

* cited by examiner

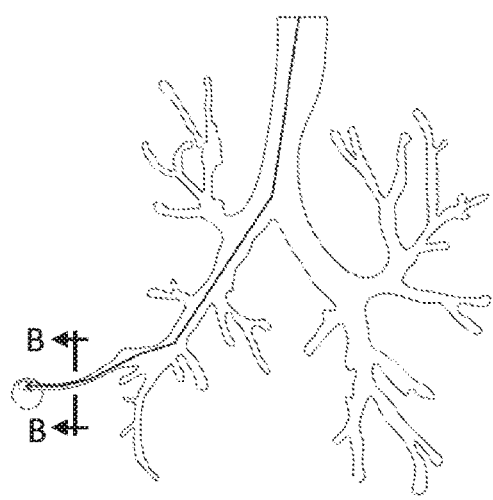
FIG. 4A
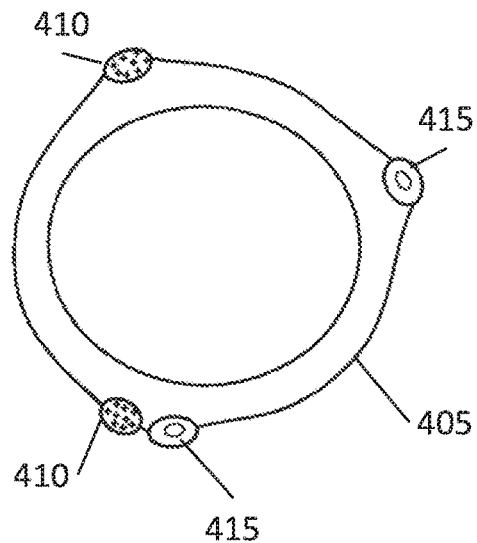
FIG. 4B
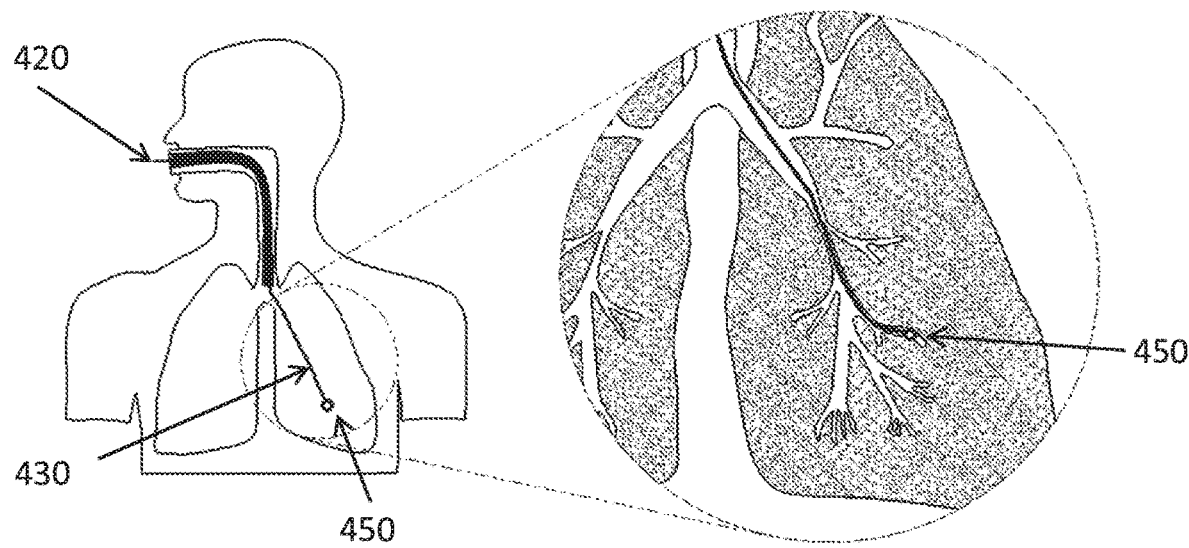
FIG. 4C
FIG. 4D

SYSTEM AND METHOD FOR LUNG VISUALIZATION USING ULTRASOUND

CROSS-REFERENCE TO RELATED APPLICATIONS

The present application is a continuation of U.S. patent application Ser. No. 14/469,728 filed on Aug. 27, 2014, now U.S. Pat. No. 10,098,566, which claims priority to U.S. Provisional Application No. 61/874,881 filed on Sep. 6, 2013, U.S. Provisional Application No. 62/041,850 filed on Aug. 26, 2014, and U.S. Provisional Application No. 62/041,842 filed on Aug. 26, 2014, the entire contents of each of which are incorporated herein by reference.

BACKGROUND

Technical Field

The present disclosure relates to systems and methods for visualizing a lung using ultrasound imaging techniques. More particularly, the present disclosure relates to systems and methods that augment images of a luminal networks obtained by other imaging modality with ultrasound images.

Discussion of Related Art

Standard of care for lung diseases, such as asthma, chronic obstructive pulmonary disease (COPD), and chronic obstructive lung disease (COLD), or for lung-related diseases has been focused largely on medical and/or drug management which are highly invasive to patients in general. For example, it has been reported for decades that lung denervation via localized and invasive means (e.g., surgery) may provide therapeutic benefit for asthma or emphysema.

Electromagnetic navigation (EMN) has helped expand the possibilities of treatment of luminal networks such as the lungs. EMN relies on non-invasive imaging technologies, such as computed tomography (CT) scanning, magnetic resonance imaging (MRI), or fluoroscopic technologies. EMN in combination with these non-invasive imaging technologies has been also used to identify a location of a target and to help clinicians navigate a luminal network of the lung to the target. However, images generated by these non-invasive imaging technologies have been unable to provide a resolution sufficient to identify features such locations of nerves that run parallel to the luminal network. Further, when a treatment is performed, additional images using these non-invasive imaging technologies must have been performed to determine whether the treatment has been complete. That increases the number of exposures of harmful X-rays or substances to the patient and costs of treatments. Still further, every clinician is desirous of a greater resolution of the area being treated. Accordingly there is a need for an imaging modality, which provides the desired resolution and is clinically efficient in operation.

SUMMARY

In an aspect, the present disclosure features a method for US based interrogation of a lung. The method includes importing a three dimensional (3D) model of a luminal network and a pathway plan to a target into a navigation system, generating an electromagnetic (EM) field about a luminal network, inserting an EM sensor and a US transducer into the luminal network following the pathway plan toward the target, sensing, at the EM sensor, the EM field, synchronizing a location of the EM sensor in the EM field with the 3D model, transmitting, at the US transducer, US waves, receiving, at the US transducer, reflected US waves, and predicting based on the reflected US waves a type, density, disease state, or sufficiency of treatment of tissue reflecting the US waves.

In another aspect, the system further includes calculating a scale factor between a coordinate system of the EM field and a coordinate system of the 3D model. The method still further includes scaling a traveled distance of the EM sensor to synchronize movement of the EM sensor in the 3D model based on the pathway plan and the scale factor.

In another aspect, the method further includes processing the reflected US waves to generate US images. The method still further includes integrating the generated US images with the 3D model. The method still further includes displaying the integrated 3D model and US images based on the location of the EM sensor. A resolution of the generated US image is finer than a resolution of the 3D model. The generated image shows tissue outside of the luminal network.

In yet another aspect, the method further includes calculating a distance between the location of the EM sensor and a location of the US transducer. Integrating the generated US images with the 3D model is based on the calculated distance.

In another aspect, the method further includes displaying a status based on the location of the EM sensor. The status indicates whether the EM sensor is located at a not-in-target location, the target, or a location adjacent to healthy tissue. The status also indicates whether treatment of the target is complete.

In another aspect, the method further includes determining whether a size of the target after treatment is less than or equal to a predetermined size. The method still further includes displaying a notice notifying the sufficiency of treatment of the target based on a determination of the size of the target after treatment.

In another aspect, the method is further includes identifying a new target while following the pathway plan toward the target based on the reflected US waves. The method still further includes registering the new target to the 3D model or adding the new target to the pathway plan.

In yet another aspect, the method further includes recognizing a breathing pattern of a patient. The method still further includes identifying the location of the EM sensor by compensating for patient's breathing based on the breathing pattern.

Any of the above aspects and embodiments of the present disclosure may be combined without departing from the scope of the present disclosure.

BRIEF DESCRIPTION OF THE DRAWINGS

Objects and features of the presently disclosed systems and methods will become apparent to those of ordinary skill in the art when descriptions of various embodiments are read with reference to the accompanying drawings, of which:

FIG. 4A is an illustration of a pathway from the entry point to the target in accordance with an embodiment of the present disclosure;

FIG. 4B is a transverse cross-sectional view of the section of the lung of FIG. 4A taken along section line B-B;

FIG. 4C is an illustration of a catheter guide assembly inserted into a lung following the pathway plan of FIG. 4A;

FIG. 4D is an enlarged detail view of the circled area of FIG. 4C;

DETAILED DESCRIPTION

The present disclosure is related to systems and methods for visualizing the luminal network of a lung using ultrasound (US) imaging technologies which provide a sufficient resolution to identify and locate a target for diagnostic, navigation, and treatment purposes. US imaging, particularly in conjunction with non-invasive imaging can provide a greater resolution and enable luminal network mapping and target identification. Further, additional clarity is provided with respect to tissue adjacent identified targets which can result in different treatment options being considered to avoid adversely affecting the adjacent tissue. Still further, the use of US imaging in conjunction with treatment can provide detailed imaging for post treatment analysis and identification of sufficiency of treatment. Although the present disclosure will be described in terms of specific illustrative embodiments, it will be readily apparent to those skilled in this art that various modifications, rearrangements, and substitutions may be made without departing from the spirit of the present disclosure. The scope of the present disclosure is defined by the claims appended to this disclosure.

Figure 1:
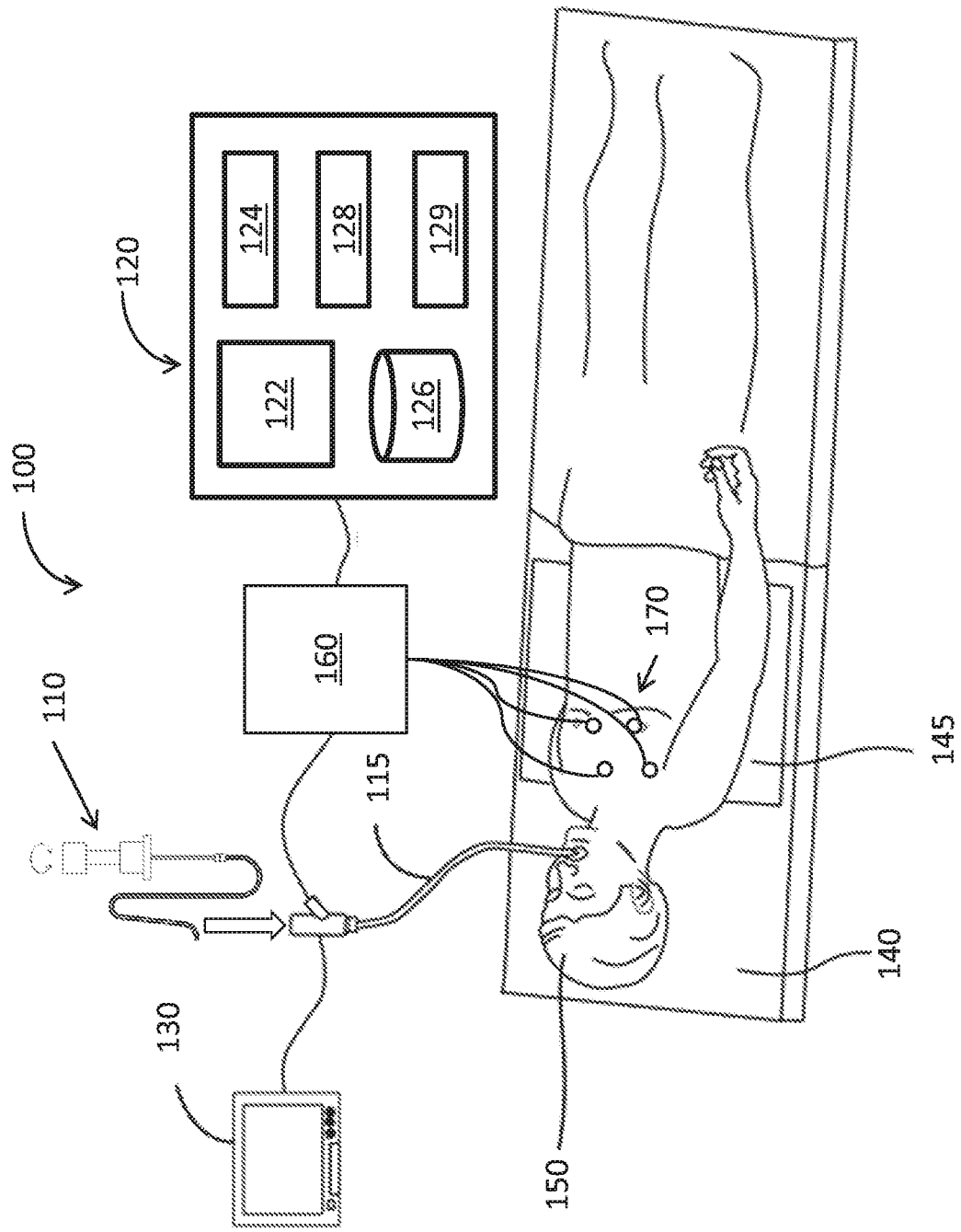
FIG. 1 is a perspective view of a system for visualizing a lung of a patient in accordance with an embodiment of the present disclosure.

FIG. 1 illustrates an electromagnetic navigation (ENM) system 100, which is configured to augment CT, MRI, or fluoroscopic images, with US image data assisting in navigation through a luminal network of a patient's lung to a target. One such ENM system may be the ELECTROMAGNETIC NAVIGATION BRONCHOSCOPY® system currently sold by Covidien LP. The system 100 includes a catheter guide assembly 110, a bronchoscope 115, a computing device 120, a monitoring device 130, an EM board 140, a tracking device 160, and reference sensors 170. The bronchoscope 115 is operatively coupled to the computing device 120 and the monitoring device 130 via wired connection (as shown in FIG. 1) or wireless connection (not shown).

The bronchoscope 115 is inserted into the mouth of the patient 150 and captures images of the luminal network of the lung. In the EMN system 100, inserted into the bronchoscope 115 is a catheter guide assembly 110 for achieving access to the periphery of the luminal network of the patient 150. The catheter guide assembly 110 may include an extended working channel (EWC) 230 into which a locatable guide catheter (LG) 220 with EM sensor 265 (FIG. 2B) at the distal tip is inserted. EWC 230, the LG 220, and an EM sensor 265 are used to navigate through the luminal network of the lung as described in greater detail below.

The computing device 120, such as, a laptop, desktop, tablet, or other similar computing device, includes a display 122, one or more processors 124, memory 126, a network card 128, and an input device 129. The system 100 may also include multiple computing devices, wherein the multiple computing devices 120 are employed for planning, treatment, visualization, or helping clinicians in a manner suitable for medical operations. The display 122 may be touch-sensitive and/or voice-activated, enabling the display 122 to serve as both an input and output device. The display 122 may display a two dimensional (2D) images or three dimensional (3D) model of a lung to locate and identify a portion of the lung that displays symptoms of lung diseases. The generation of such images and models is described in greater detail below. The display 122 may further display options to select, add, and remove a target to be treated and settable items for the visualization of the lung. In an aspect, the display 122 may also display the location of the catheter guide assembly 110 in the luminal network of the lung based on the 2D images or 3D model of the lung. For ease of description not intended to be limiting on the scope of this disclosure, a 3D model is described in detail below but one of skill in the art will recognize that similar features and tasks can be accomplished with 2D models and images.

The one or more processors 124 execute computer-executable instructions. The processors 124 may perform image-processing functions so that the 3D model of the lung can be displayed on the display 122. In embodiments, the computing device 120 may further include a separate graphic accelerator (not shown) that performs only the image-processing functions so that the one or more processors 124 may be available for other programs.

The memory 126 stores data and programs. For example, data may be image data for the 3D model or any other related data such as patients' medical records, prescriptions and/or history of the patient's diseases. One type of programs stored in the memory 126 is a 3D model and pathway planning software module (planning software). An example of the 3D model generation and pathway planning software may be the ILOGIC® planning suite currently sold by Covidien LP. When image data of a patient, which is typically in digital imaging and communications in medicine (DICOM) format, from for example a CT image data set (or image data set by other imaging modality) is imported into the planning software, a 3D model of the bronchial tree is generated. In an aspect, imaging may be done by CT imaging, magnetic resonance imaging (MRI), functional MRI, X-ray, and/or any other imaging modalities. To generate the 3D model, the planning software employs segmentation, surface rendering, and/or volume rendering. The planning software then allows for the 3D model to be sliced or manipulated into a number of different views including axial, coronal, and sagittal views that are commonly used to review the original image data. These different views allow the user to review all of the image data and identify potential targets in the images.

Once a target is identified, the software enters into a pathway planning module. The pathway planning module develops a pathway plan to achieve access to the targets and the pathway plan pin-points the location and identifies the coordinates of the target such that they can be arrived at using the EMN system 100, and particularly the catheter guide assembly 110 together with the EWC 230 and the LG 220. The pathway planning module guides a clinician through a series of steps to develop a pathway plan for export and later use in during navigation to the target in the patient 150. The term, clinician, may include doctor, surgeon, nurse, medical assistant, or any user of the pathway planning module involved in planning, performing, monitoring and/or supervising a medical procedure.

Details of these processes and the pathway planning module can be found in concurrently filed with this disclosure and commonly assigned U.S. Patent Application No. 62/035,863 filed Aug. 11, 2014 entitled "Treatment procedure planning system and method" and U.S. patent application Ser. No. 13/838,805 filed by Covidien LP on Jun. 21, 2013, and entitled "Pathway planning system and method," the entire contents of each of which are incorporated in this disclosure by reference. Such pathway planning modules permit clinicians to view individual slices of the CT image data set and to identify one or more targets. These targets may be, for example, lesions or the location of a nerve which affects the actions of tissue where lung disease has rendered the lung function compromised.

The memory 126 may store navigation and procedure software which interfaces with the EMN system 100 to provide guidance to the clinician and provide a representation of the planned pathway on the 3D model and 2D images derived from the 3D model. An example of such navigation software may be the ILOGIC® navigation and procedure suite sold by Covidien LP. In practice, the location of the patient 150 in the EM field generated by the EM field generating device 145 must be registered to the 3D model and the 2D images derived from the model.

Such registration may be manual or automatic and is described in detail in concurrently filed with this disclosure and commonly assigned U.S. Patent Application 62/020,240 filed by Covidien LP on Jul. 2, 2014, and entitled "System and method for navigating within the lung."

As shown in FIG. 1, the EM board 140 is configured to provide a flat surface for the patient to lie down and includes an EM field generating device 145. When the patient 150 lies down on the EM board 140, the EM field generating device 145 generates an EM field sufficient to surround a portion of the patient 150. The EM sensor 265 at the distal tip 260 of the LG 220 is used to determine the location of the EM sensor 265 in the EM field generated by the EM field generating device 145.

In embodiment, the EM board 140 may be configured to be operatively coupled with the reference sensors 170 which are located on the chest of the patient 170. The reference sensors 170 move up and down following the chest while the patient 150 is inhaling and move down following the chest while the patient 150 is exhaling. The movement of the reference sensors 170 in the EM field is captured by the reference sensors 170 and transmitted to the tracking device 160 so that the breathing pattern of the patient 150 may be recognized. The tracking device 160 also receives outputs of the EM sensor 265, combines both outputs, and compensates the breathing pattern for the location of the EM sensor 265. In this way, the location identified by the EM sensor 265 may be compensated for so that the compensated location of the EM sensor 265 is synchronized with the 3D model of the lung. Once the patient 150 is registered to the 3D model, the position of the EWC 230 and particularly the LG 220 can be tracked within the EM field generated by the EM field generator 145, and the position of the LG 220 can be depicted in the 3D model or 2D images of the navigation and procedure software.

Figure 2A:
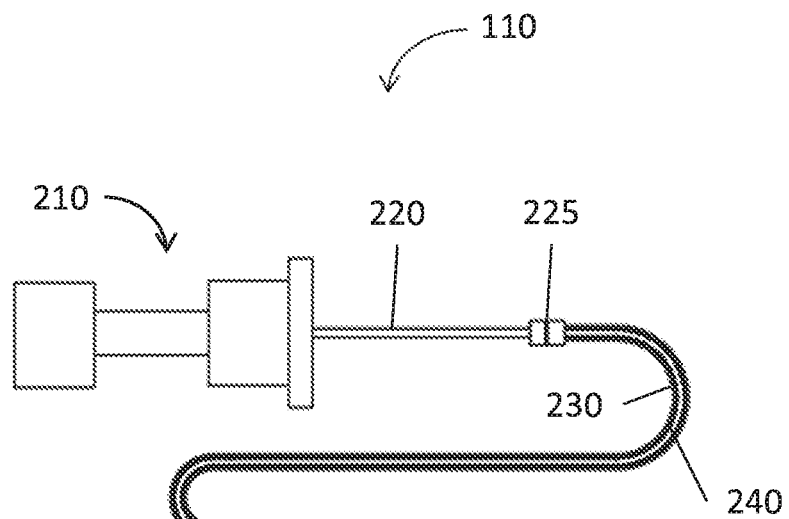
FIG. 2A is a profile view of a catheter guide assembly in accordance with an embodiment of the present disclosure.

FIG. 2A illustrates an embodiment of the catheter guide assembly 110 of FIG. 1. The catheter guide assembly 110 includes a control handle 210. The control handle 210 has an actuator and a selector mechanism for selectively mechanically steering, rotating, and advancing an extended working channel (EWC) 230 or locatable guide catheter (LG) 220 inserted in the EWC 230, meaning that the distal tip 260 of the LG 220 is turning to a direction in accordance with the movement of the control handle 210. A locking mechanism 225 secures the EWC 230 and the LG 220 to one another. Catheter guide assemblies usable with the instant disclosure are currently marketed and sold by Covidien LP under the name SUPERDIMENSION® Procedure Kits and EDGE™ Procedure Kits. For a more detailed description of the catheter guide assemblies is made to commonly-owned U.S. patent application Ser. No. 13/836,203 filed on Mar. 15, 2013 by Ladtkow et al. and U.S. Pat. No. 7,233,820, the entire contents of which are hereby incorporated by reference.

Figure 2B:
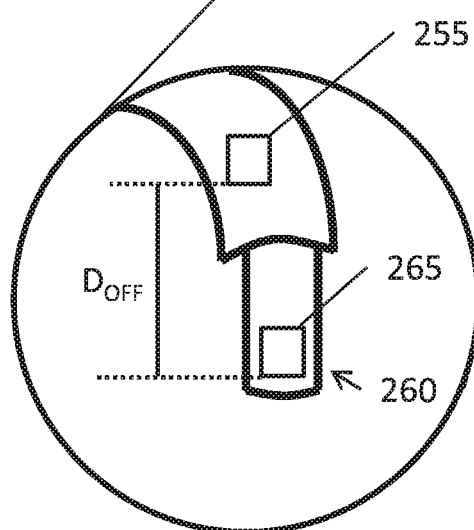
FIG. 2B is an expanded view of the indicated area of detail, which shows a distal tip of an extended working channel of FIG. 2A in accordance with an embodiment of the present disclosure.

FIG. 2B is an expanded view of the distal end 250 of the EWC 230 of FIG. 2A. A US transducer 265 located at the distal end 250 of the EWC 230. The EM sensor 265 is located at the distal tip 260 of the LG 220, which is depicted extending beyond the distal end 250 of the EWC 230. As described briefly above, the EM sensor 265 senses the EM field generated by the EM field generating device 145. The sensed EM field is used to identify the location of the EM sensor 265 in accordance with the coordinate system of the EM field. When the location of the EM sensor 265 is determined by the tracking device 160, the computing device 120 compares the location of the EM sensor 265 with the 3D model of the lung and registers the location of the EM sensor 265 into the coordinate system of the 3D model.

For example, when the EM sensor 265 is near at the entrance to the trachea, the EM sensor 265 senses the EM field and the location of the EM sensor is then compared with the trachea portion of the 3D model so that the location of the EM sensor 265 is depicted in the corresponding location of the 3D model and 2D images of the navigation and procedure software. And when the EM sensor 265 is further inserted through the trachea to a location where separate bronchial trees are branched, the distance the EM sensor 265 travels from the entrance of the trachea to the branching location is scaled to match to the corresponding distance in the 3D model and 2D images of the navigation and procedure software. Specifically, when the EM sensor 265 travels along the trachea, the distance is measured in accordance with the coordinate system of the EM field. Since the coordinate system of the EM field is different from the coordinate system of the 3D model, there is a scaling factor to match the coordinate system of the EM field to the coordinate system of the 3D model. Thus, by multiplying a scale factor to the distance the EM sensor 265 travels, the coordinate system of the EM field is synchronized with the coordinate system of the 3D model. In this way, the EM field may be synchronized with the 3D model and 2D images of the navigation and procedure software. Or other suitable method may be employed to synchronize the coordinate system of the EM field with the coordinate system of the 3D model.

As noted above, the 3D model may not provide a resolution sufficient for guiding the EWC 230 of the catheter guide assembly 110 to a target, meaning that the 3D model becomes blurred or ceases to recognize the luminal network as the EWC 230 approaches a certain point. For example, when CT scan images are taken by 1 mm thick and 1 cm apart by a CT scan device, corresponding 3D model and/or pathway plans may not be able to show full perspective of a target whose size is less than 1 cm or a portion of a luminal network whose diameter is less than 1 cm. Thus, another imaging modality is necessary to find and/or identify a target and/or a terminal bronchial branch, whose size is less than a certain size which CT scan images are unable to show with sufficient details. For this purpose, the memory 126 also stores another program that can process and convert image data captured by an imaging modality associated with the catheter guide assembly 110, as will be described in detail below. This image data may be converted into visual images having sufficient resolutions to identify such targets and terminal bronchial branches or be incorporated into and used to update the data from the CT scans in an effort to provide a greater resolution and fill-in data that was missing in the CT scan.

One such imaging modality is depicted in FIG. 2B where the US transducer 255 is depicted on the EWC 230 proximal the distal end. One of skill in the art will recognize that the location of the US transducer 255 and the EM sensor 265 may be alternated between the LG 220 and the EWC 230, or that more than one of each sensor and transducer may be employed without departing from the scope of the present disclosure. The US transducer 255 transmits ultrasound waves and receives reflected ultrasound waves. Generally, ultrasound waves penetrate tissue based on the frequency of the ultrasound waves. For example, 1 megahertz (MHz) ultrasound waves penetrate to a depth of 2 cm to 5 cm and 3 MHz ultrasound waves penetrate to a depth of 1.5 cm. Thus, US waves are suitable for imaging bronchial trees. In an aspect, the US transducer 255 may be a radial US transducer.

Generally, US waves are reflected at a boundary where density changes or at the interface between tissues. While the US transducer 255 is navigating the luminal network of the lung, the US waves are reflected from the inside wall of a bronchial tree, from the outside wall of the bronchial tree, and from a diseased portion or cancerous portion located at the outside wall of the bronchial tree and provide finite details of the lung structure and the tissue patency that could not otherwise be revealed using non-invasive imaging means.

The reflected US waves have information such as amplitude and a delayed time between transmission of the US waves and reception of the reflected US waves. Since the US waves travels differently and attenuates amplitudes differently in accordance with the density of tissue, the amplitude and the delayed time may be used to identify a type of tissue, a density of the tissue, and/or a size of the tissue. Since the density of abnormal tissues (e.g., diseased or cancerous cells) are different from the normal lung tissue, the reflected US waves may be used to identify the diseased or cancerous cells from normal cells and the size and/or thickness of the diseased or cancerous cells.

The computing device 120 analyzes the reflected US waves and generates visual images which has a higher resolution than that of the 3D model or the CT scan images. The generated visual images may be augmented to and integrated with the 3D model of the lung or 2D images such as the CT scan images.

In embodiments, when a treatment is performed to treat an abnormal tissue located at the outside wall of a bronchial tree, generally, the size of the abnormal tissue shrinks and density of the abnormal tissue changes to the density of the normal lung tissue. Traditionally, when a treatment is performed, another CT scan is performed to obtain another set of CT images to check the size of the diseased or cancerous cells so that clinicians may determine whether the treatment is complete or another one is to be made. Since the US transducer 255 is able to check the size and the density of the abnormal tissue, the level of treatment may also be checked at the spot without performing another CT scan.

As shown in FIG. 2B, the US transducer 255 and the EM sensor 265 are separated by a distance, $D_{OFF}$. This distance, $D_{OFF}$, may be sensed, coded into the navigation and procedure software, measured and sent by the clinician, or sensed by the US transducer 255 and the EM sensor 265. The computing device 120 uses the distance, $D_{OFF}$, to adjust the incorporation of the US images into the 3D model or 2D images derived therefrom. For example, when the EM sensor 265 is located at the distal tip 260 of the LG 220, the US transducer 255 is located at or circumscribing the distal end 250 of the EWC 230, and both sensors are 1 cm distance apart from each other, this distance is recognized by the software and the US data or images is offset and integrated into the 3D model or 2D images derived therefrom by a distance in the coordinate system of the 3D model, which corresponds to 1 cm in the coordinate system of the EM field.

When the EWC 230 and the LG 220 reaches a target by manipulation of the catheter guide assembly 110 following the pathway plan, the EM sensor 265 confirms its location at the target and a clinician may visually confirm the location at the target by looking at visual images generated from the US images. The LG catheter 220 may be removed from the catheter guide assembly 110 and a biopsy tool may be inserted into the EWC 230 to the target to retrieve sample of the target for confirmation of the disease. An anchoring tool may be employed to anchor the EWC 230 at the target. Further, treatment tools such as an ablation catheter may be inserted through the EWC 230 and into the target. The US transducer 255 may then be used to transmit and receive US waves and the computing device 120 determines whether the treatment tool is at the epicenter of the target by comparing the densities of the tissue surrounding the treatment tool or by generating US images of the target for clinical comparison. By being located at the epicenter of the target, the treatment tool may perform treatment with high efficiency. In an aspect, the EM sensor 265 and the US transducer 255 may be located at or around the EWC 230 with a distance apart from each other or at or around the LG 220 with a distance apart from each other.

In embodiments, the US transducer 255 and the computing device 120 may check the size of the target either before or after treatment. When the size of the target is greater than a threshold size, another treatment may be necessary to complete the treatment. Thus, the treatment continues until the size of the target is decreased under the threshold size. In this way, visualization using US waves may be utilized for checking the level of treatment.

In embodiments, the US transducer 255 may be a sacrificial US transducer 255 which may be positioned in a forward looking manner to identify the target. The US transducer 255 is sacrificial because it may be rendered ineffective following treatments of the target by the application of microwave energy of the treatment device.

In embodiments, in a pre-treatment step, one or more markers can be placed through the EWC 230 to identify the location of the target. The marker may assist in navigating to a desired location and confirming placement of the EWC 230, particularly after removal of the LG 220 and the EM sensor 265 when the EM navigation features of the present disclosure may not be effective. The marker may give a clinician an ability to re-visit the target after the target has been treated and to collect further samples. The marker may be a fiducial marker, fluorescent dye, or FLUOROGOLD®.

In the case of fluorescent dye markers, the US imaging capabilities may further increase the determination of sufficiency of treatment, or provide greater clarity as to the exact location of the target. Other markers for marking the location of a target may be employed by those of ordinary skill in the art without departing from the scope of the present disclosure.

Figure 3:
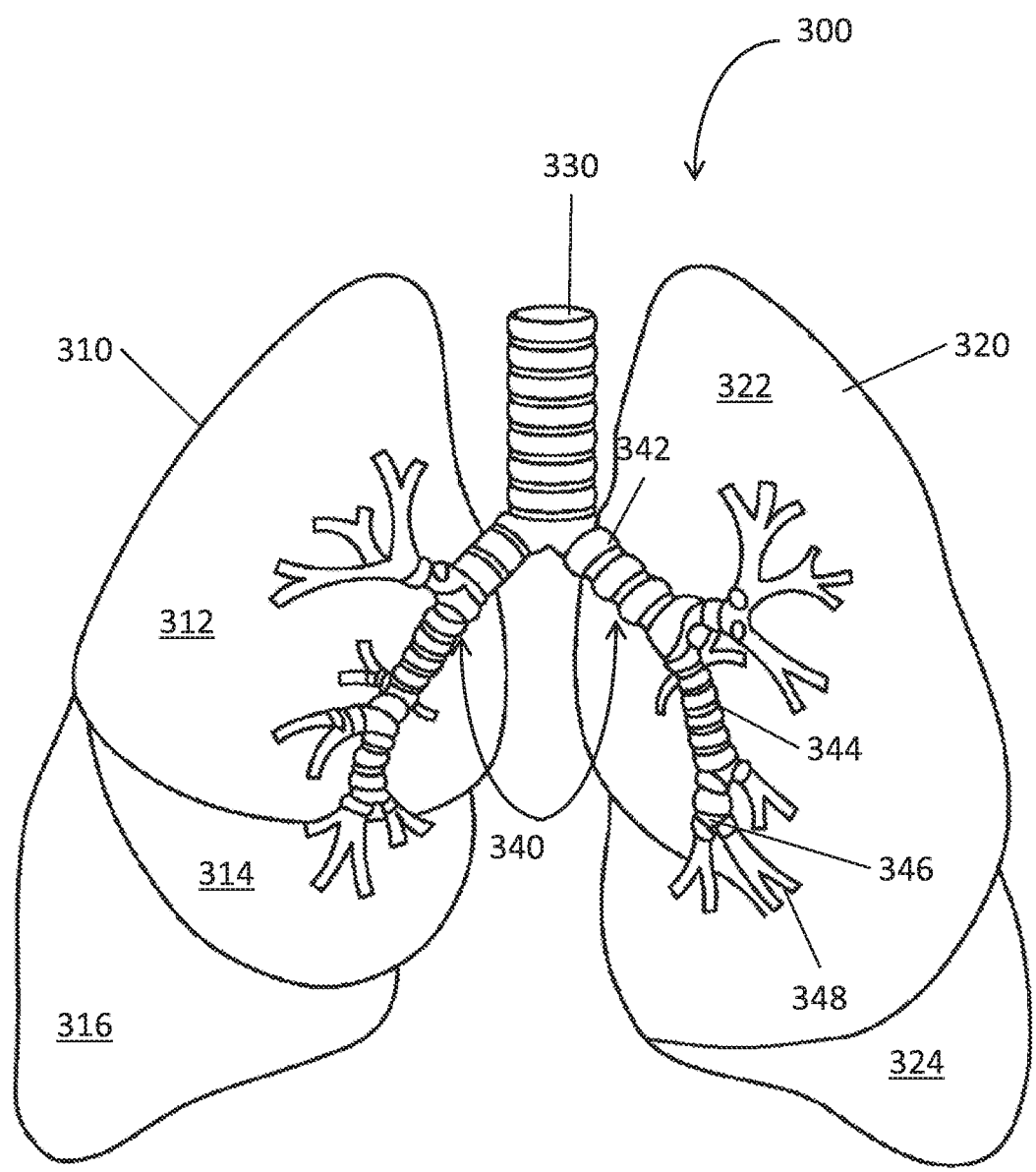
FIG. 3 is an anatomical illustration of a three dimensional model for a lung in accordance with an embodiment of the present disclosure.

FIG. 3 illustrates a 3D model 300 for a patent's bronchial trees and the trachea together with the lung. The 3D model 300 may include information of most of the organs so that a clinician may selectively see particular organs or portions of organs of interest as shown in FIG. 3. In this case, these selected organs are the lungs including right lobe 310, the left lobe 320, the trachea 330 and bronchial trees 340. The right lobe 310 has three sub-lobes, i.e., superior lobe 312, middle lobe 314, and inferior lobe 316, and the left lobe 320 has two sub-lobes, i.e., superior lobe 322 and inferior lobe 324.

The trachea 330 is a tube that connects the pharynx and larynx to the lung 310 and 320. At the lower end of the trachea 330, left or right primary bronchus 342 is divided. Secondary bronchus 344 also divides at the lower end of the primary bronchus 342. The circumference of the primary bronchus 342 is greater than that of the secondary bronchus 344. In the same manner, tertiary bronchus 346 divides at the lower end of the secondary bronchus 344 and terminal bronchiole 348 divides at the lower end of the tertiary bronchus 346. The primary bronchus 342, the secondary bronchus 344, and the tertiary bronchus 346 are supported by cartilaginous plates. However, when the size of the tertiary bronchus 346 becomes smaller and smaller, the cartilaginous plates disappear and outer wall is dominated by smooth muscle. The outer wall of the terminal bronchiole 348 is also dominated by smooth muscle.

Diseased or cancerous cells or simply a target may exist on any bronchial trees, the primary bronchus 342, the secondary bronchus 344, the tertiary bronchus 346, and the terminal bronchioles 348. No matter where a target is located, when a target is too small to be detected by a CT imaging modality, the target may still be detected by the US imaging modality while the EWC 230 with US transducer 255 is navigating toward another target through the luminal network of the lung. The US transducer 255 provides greater specificity and greater accuracy in detecting and identifying a target's location in the patient. In accordance with at least one embodiment, the US transducer 255 may be a radial ultrasound transducer employed to further refine the image data of the lungs by following the pathway plan described above and capturing US image data along the pathway. This US image data may be registered to the CT scan images and/or the 3D model 300 to provide greater clarity with respect to the detection, location, and size of a target. For example, this data may also be used diagnostically to help the clinician confirm that all likely targets have been identified or treated completely after treatments.

In addition, when the US transducer 255 captures image data the captured image data is transferred to the computing device 120 wirelessly or via a wired connection. Image data captured by an ultrasound imaging modality, is not yet readily apprehended by a clinician. The computing device 120 processes and converts it to an image with which a clinician can identify a type of tissue, diagnose a disease, identify a location of the catheter guide assembly 110, which is the place of image taking, or determine a level of treatment.

FIG. 4A shows a planar view of bronchial trees of the 3D model or of the slices of images of the lung such as the bronchial trees of FIG. 3 and a pathway plan to a target. When a target is located at the tip of the bottom left end of the terminal bronchiole of FIG. 3, a pathway plan shows how to get to the target via the luminal network of the lung.

FIG. 4B shows an expanded transverse cross-sectional view of the terminal bronchiole of FIG. 4A taken along section line B-B. The terminal bronchiole is surrounded by smooth muscle 405. Nerves 410 and veins 415 are located on the outer wall of the smooth muscle 405. The US imaging modality, as described above, provides a local view of the airways even out to the terminal bronchiole so that even the thin nerves 410 and the veins 415 on the smooth muscle 405 can be detected and identified. Thus, by using US imaging in addition to the CT imaging, navigation to and direction of therapies such as denervation can be accomplished even at the lung periphery enabling greater granularity of treatment options and with greater precision.

FIG. 4C illustrates a bronchoscope 420 with a catheter guide assembly inserted into the lungs via a natural orifice (e.g., the mouth) of a patient toward the target following a pathway plan. When the bronchoscope 420 reaches a certain location of the lung, the bronchoscope 420 becomes wedged and cannot go further into bronchial tree due to the size constraints. Then, the EWC 430 of the catheter guide assembly may be used to navigate the luminal network to a target 450 following the pathway plan, as described above. The EWC 430 is small and thin enough to reach the target 450. FIG. 4D illustrates an enlarged detail view of the circled area of FIG. 4C, where a locatable guide (LG) may stick out of the distal tip of the EWC 430 which navigates the luminal network to the target 450 located at the terminal bronchiole of the lung.

Figure 5A:
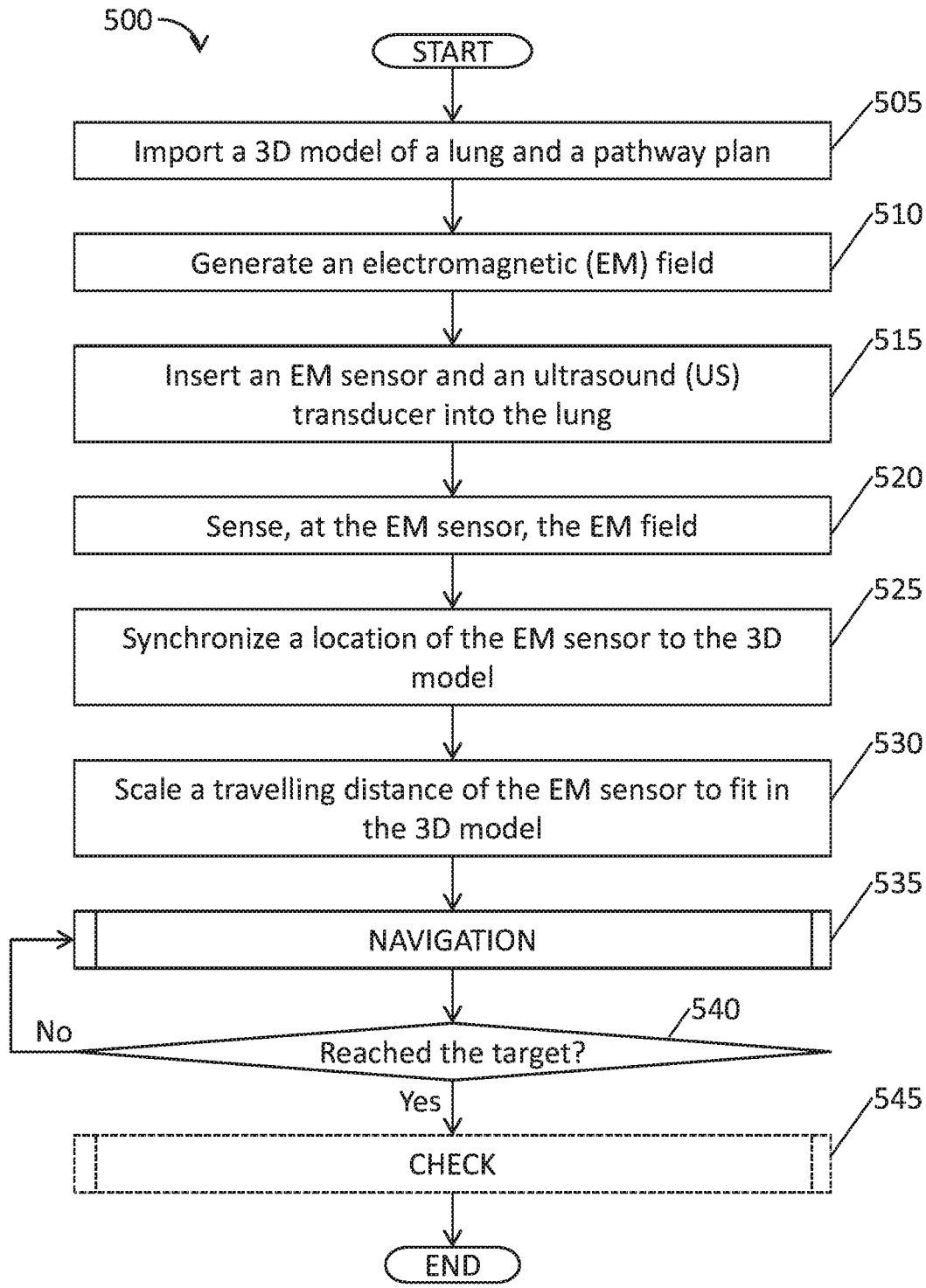
FIG. 5A is a flowchart of a method for visualizing a lung using US waves in accordance with an embodiment of the present disclosure.

FIG. 5A is a flowchart of a method 500 for visualizing a lung using US imaging technology. The method 500 starts at step 505 by importing a 3D model of a lung and a pathway plan to a target into the navigation and procedure software stored on a computer such as the computing device 120 of FIG. 1.

In step 510, an EM field is generated by an EM board, such as the EM field generating device 145 of the EM board 140 as shown in FIG. 1. In step 515, an EM sensor 265 and a US transducer 255 are inserted into the lung via a natural orifice or an incision. The EM sensor 265 and the US transducer 255 may be located on the EWC 230 with a distance apart or may be located at different places. For example, the EM sensor 265 may be located at or around the distal tip 260 of the LG 220 and the US transducer 255 may be located at or around the distal end 250 of the EWC 230, or vice versa.

In step 520, the EM sensor 265 senses the EM field and the sensed results are transmitted to the computing device 120. The sensed results are used to calculate a location of the EM sensor 265 in the coordinate system of the EM field. When the location is calculated, the computing device compares the location of the EM sensor 265 with the 3D model, the 2D images derived therefrom, and the pathway plan. In an aspect, the location of the EM sensor 265 may be compensated according to the breathing pattern of the patient by the tracking device 160 and the reference sensors 170 before transmitted to the computing device. Thus, the location of the ME sensor 255 may not vary in the coordinate system of the 3D model while the patient inhales or exhales.

In step 525, the location of the EM sensor 265 is synchronized to the 3D model and the 2D images derived therefrom. This location may be the starting location of the 3D model, or the entrance of the trachea of the 3D model.

Even though the location is synchronized, the actual movement of the EM sensor 265 is not synchronized to the 3D model yet, here.

The EM sensor 265 travels a certain distance (e.g., from the entrance of the trachea to the branching point at the bottom of the trachea). This distance may be measured in the coordinate system of the EM field after the EM sensor 265 starts to sense the EM field. In step 530, the travelling distance by the EM sensor 265 according to the coordinate system of the EM field may be scaled so that the scaled distance is matched to the coordinate system of the 3D model. After this step, the location and the movement of the EM sensor 265 are substantially mapped into the 3D model. This is the synchronization or registration of the patient to the 3D model and the 2D images derived therefrom.

In step 535, the EM sensor 265, the LG 220, and the EWC 230 navigate the luminal network of the lung to the target following the pathway plan. In step 540, it is determined whether the sensor 265 has reached the target. If it is determined that the EM sensor 265 has not reach the target, step 535, i.e., the navigation step, is continued until the target is reached following the pathway plan.

In embodiments, when it is determined that the target is reached in step 540, step 545 may be performed to image the target with the US transducer 255 to confirm its location. This may involve confirming tissue densities or confirming position relative to markers and other location confirmatory steps. In addition, imaging of the target may be employed after treatment to ensure sufficiency of treatment. Step 545 is described in further detail in FIG. 5C below.

Figure 5B:
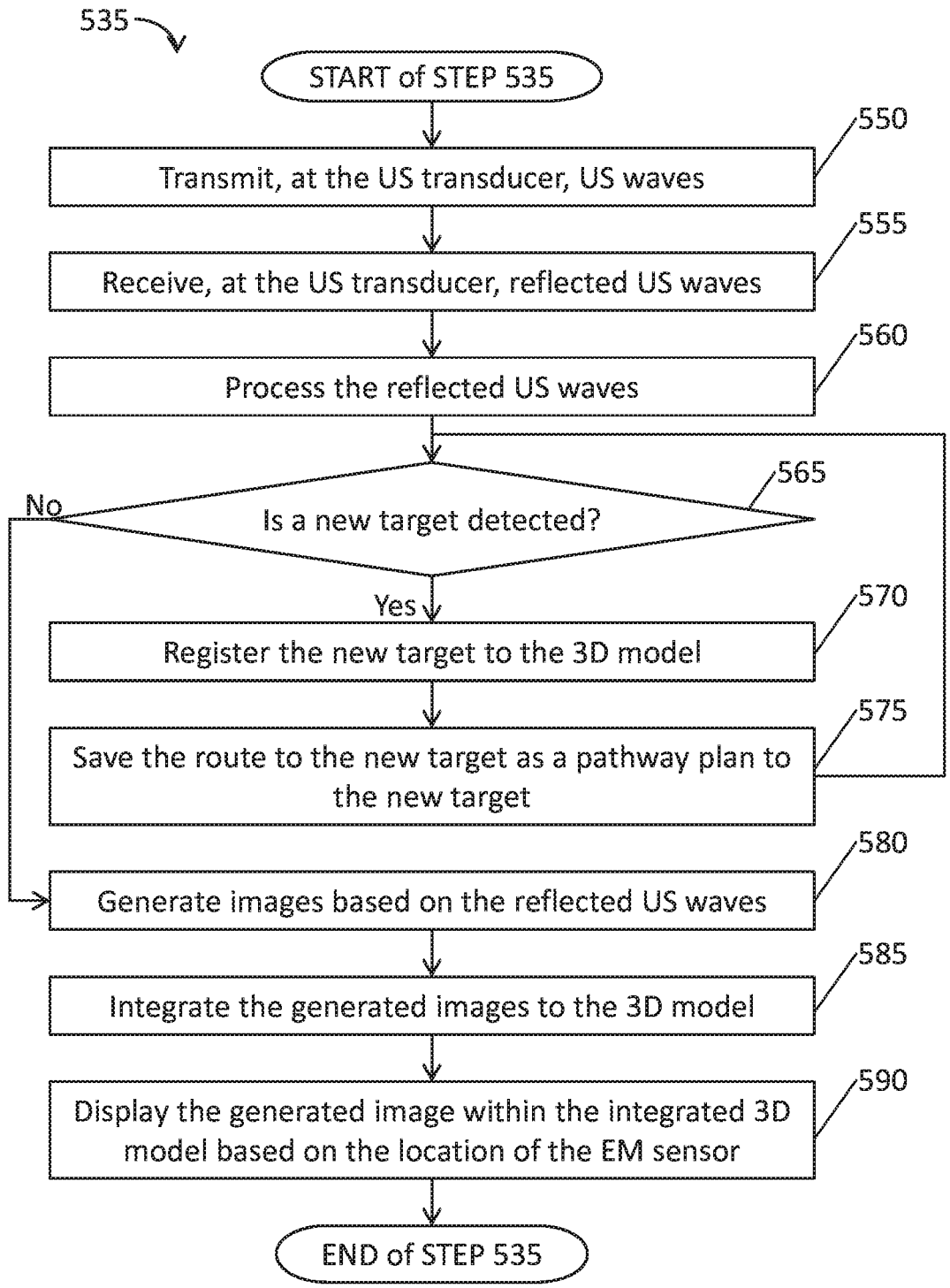
FIG. 5B is a flowchart of a method for navigation to the target in accordance with an embodiment of the present disclosure.

FIG. 5B shows detail steps of navigation to the target, step 535 of the method 500 of FIG. 5A. In step 550 US waves are transmitted by the US transducer 255 while the distal end of the EWC 230 navigates to the target following the pathway plan. In step 555, the US transducer 255 receives and sends US waves reflected from the lung tissue to the computing device 120, which in turn processes the reflected US waves in step 560. The reflected US waves have information such as amplitude and delayed time from the transmission to the reception. The computing device 120 process the information to determine the density or size of the lung tissue and/or determine whether there are new targets (i.e., diseased or cancerous cells to be treated) not found in the CT scan images.

In step 565, it is determined whether there is a new target along the pathway plan to the target. When it is determined that there is a new target, in step 570, the new target is identified and registered to the 3D model for later treatment. In step 575, the route to the new target, which is a part of the pathway plan to the target, is also saved as a pathway plan to the new target. Then, the method 535 goes back to step 565 to continue checking whether there are any further new targets.

When it is determined that there is no new target in step 565, the computing device may generate images based on the processed reflected US waves. Since the US waves are reflected from an interface between tissues where density changes, the generated images show details both inside and outside of the bronchial tree. The generated images may depict a diseased or cancerous cells residing on the outside of the bronchial tree. In an aspect, when a treatment device penetrates the target for treatment purposes, the generated images can also be used to show whether the treatment device is in the center of the target.

In step 585, the generated images are integrated into the 3D model based on the location of the EM sensor 265 and the offset distance $D_{OFF}$ between the EM sensor 265 and the US transducer 255. In embodiments, the generated images may be overlaid on CT scan images so that a lower resolution portion of the CT scan images may be replaced with a higher resolution images (i.e., the generated US images), the image data may be selectively fused to create a composite image data set, or the data can be incorporated into the CT image data. In step 590, the computing device displays the generated images with the 3D model or simply the integrated 3D model. These steps 550-590 of navigation are repeated until the target is reached as shown in the method 500 of FIG. 5A.

Figure 5C:
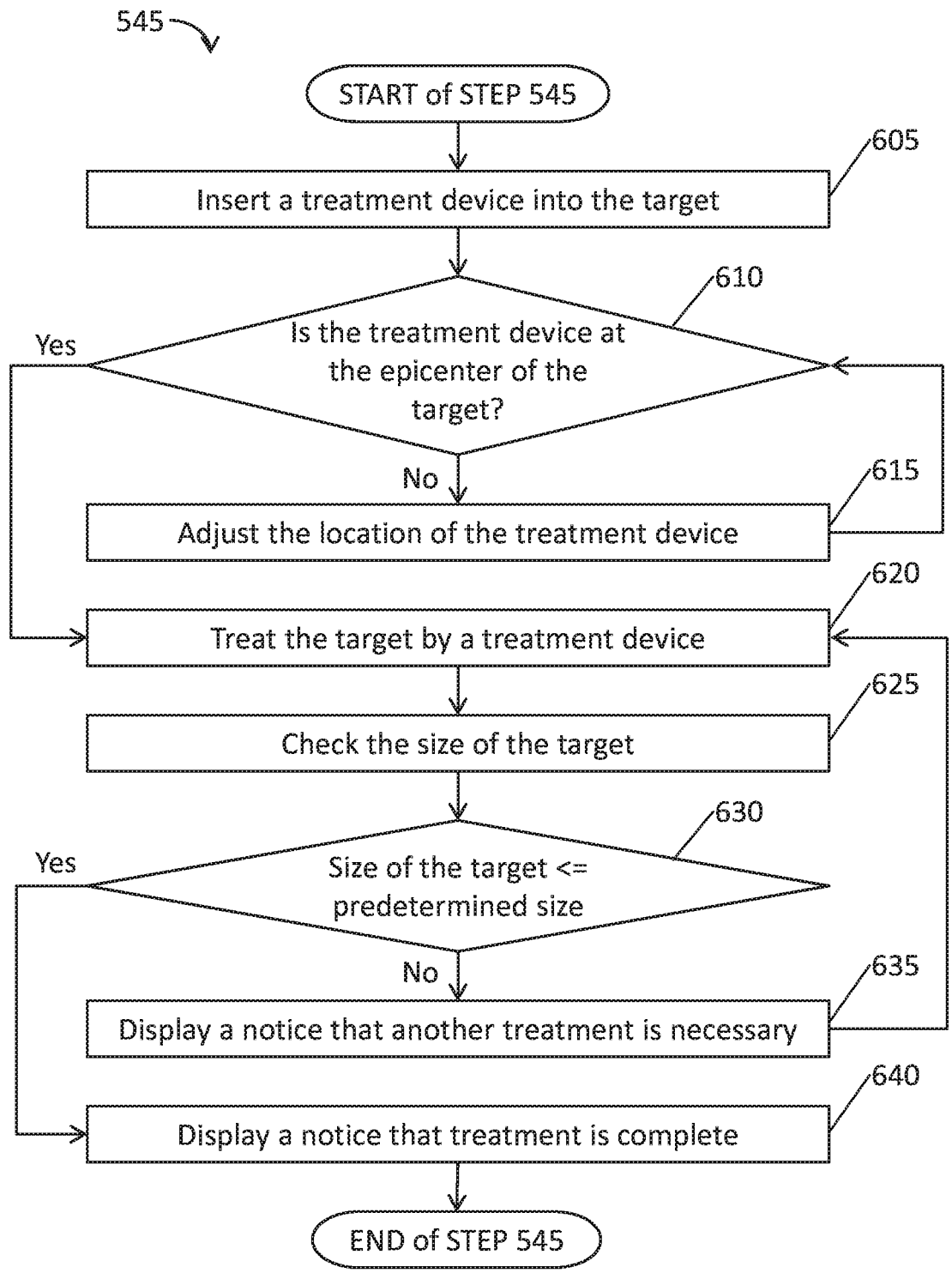
FIG. 5C is a flowchart of a method for checking the level of treatment in accordance with an embodiment of the present disclosure.

In an embodiment, visualization using the US waves may also be used to determine the sufficiency of treatment. When one treatment is performed on a target, the attributes of the target including size, density, and water content of the target is generally altered. Thus, in order to check whether the treatment is complete, the attributes of the target must be checked and compared to similar measurements taken before treatment. FIG. 5C illustrates a flowchart of a method for checking the sufficiency of treatment after it is determined that the EM sensor 265 reaches the target in step 540 of FIG. 5A. In step 605, a treatment device, such as an ablation catheter, is inserted into the EWC 230 after removal of the LG 220 and its EM sensor 265. In step 610, it is determined whether the treatment device is at the epicenter of the target. This is done by use of the US transducer 255. US images show where the density of imaged tissue changes and the target has a different density from normal lung tissue.

When it is determined that the treatment device is not at the epicenter of the target, the treatment device is inserted or retreated more or less to adjust its location in step 615. Then, in step 610, the location of the treatment device is again checked. When it is determined that the treatment device is located at the epicenter of the target in step 610, the treatment device treats the target.

In embodiments, similar steps as steps 605-615 of FIG. 5C may be applied for biopsy. When a biopsy tool is inserted to take samples of the target, the US transducer 255 is used to check whether the biopsy tool is at the correct location of the target. When it is determined that the biopsy tool is at the right place, then the biopsy tool takes samples. Or when it is determined that the biopsy tools is not at the target, the biopsy tool may be adjusted to reach correctly at the target.

In step 620, the treatment device treats the target. Following treatment application, the US transducer 255 may be employed to image the target, determine the attributes of the target in step 625 (e.g., the size), and compares the attributes of the target with threshold values in step 630. Here, the threshold size may be predetermined based on a type of disease and may indicate that the disease is treated completely.

When it is determined that the size of the treated target is greater than the threshold size, the computing device 120 notifies a clinician of incomplete treatment by displaying on the display screen such notice in step 635. The method 545 then goes back to step 620 for another treatment. These steps 620-635 repeat until the treatment is complete. In an aspect, these treatments may be performed at the spot or for a period. In a case when the treatments are performed during a period, a marker may be placed at or near the target so that a treating device can be inserted to the target with certainty during a later treatment.

When it is determined that the size of the target is less than or equal to the threshold size in step 630, the computing device 120 notifies a clinician of complete treatment by displaying that the treatment is complete in step 640, and the method 545 of checking the level of treatment is ended. Thus, the US transducer 255 and US imaging features of the present disclosure may be employed to confirm the sufficiency of treatment of a target.

In another embodiment, the monitoring device 130 and/or the computer 120 may display a color code on the display, notifying a clinician of a status. The status may be based on a location of the EWC 230 of the catheter guide assembly 110. The status may indicate whether the distal end of the EWC 230 is located at a not-in-target location, at the target, or at a location adjacent to healthy tissue, and whether treatment of the target is complete. For example, the color code may be used in a way that a red color indicates that the EWC 230 is at a not-in-target location, a green color indicates that the EWC 230 is at a target, a yellow color indicates that the EWC 230 is adjacent to healthy tissue, and an orange color indicates that the treatment is complete. However, this is an example and is not meant to limit the scope of this disclosure. Other status indication systems may be employed as people in the ordinary skill in the art would apprehend.

Though not described in detail above, with respect to FIG. 1, the network interface 128 enables other computing devices 120, the bronchoscope 115, and the catheter guide assembly 110 to communicate through a wired and/or wireless network connection. In FIG. 1, the bronchoscope 115 and catheter guide assembly 110 may transmit or receive medical images, medical data, and control data to and from the computing device 120 via a wired connection. In a case where the network interface 128 connects to other computing devices or the bronchoscope 115 and catheter guide assembly 110 wirelessly, the network interface 128 uses a frequency for communication, which may be different from the frequency the bronchoscope 115 or the catheter guide assembly 110 uses for transmitting the captured images.

The memory 126 of computing device 120 may include one or more among solid-state storage devices, flash memory chips, mass storage, tape drive, or any computer-readable storage medium which is connected to a processor through a storage controller and a communications bus. Computer readable storage media include non-transitory, volatile, non-volatile, removable, and non-removable media implemented in any method or technology for storage of information such as computer-readable instructions, data structures, program modules or other data. For example, computer-readable storage media includes random access memory (RAM), read-only memory (ROM), erasable programmable read only memory (EPROM), electrically erasable programmable read only memory (EEPROM), flash memory or other solid state memory technology, CD-ROM, DVD or other optical storage, magnetic cassettes, magnetic tape, magnetic disk storage or other magnetic storage devices, or any other medium which can be used to store desired information and which can be accessed by the computing device 120.

In embodiments, the display 122 may work as an input device such that the display 122 may receive multiple finger actions, such as pinching or spreading fingers. For example, when fingers are pinched, the portion of the displayed image, where the fingers are located on the display 122 before pinching, may be zoomed out and, when fingers are spread, the portion of the lung, where the fingers are located on the display 122 before spreading, is zoomed in. Or when multiple fingers swipe the display 122 together in one direction, the displayed image may be rotated in the same direction as the swiping direction and the amount of rotation is proportional to a distance and/or a speed of the swiping motion. These features may be also implemented using the input device 129.

The input device 129 is used for inputting data or control information, such as setting values, or text information. The input device 129 includes a keyboard, mouse, scanning devices, or other data input devices. The input device 129 may be further used to manipulate displayed images or the 3D model to zoom in and out, and rotate in any direction.

The monitoring device 130 is operatively connected with the bronchoscope 115 and the computing device 120. The monitoring device 130 includes buttons and switches for setting settable items of the monitoring device 130. The monitoring device 130 may be touch-sensitive and/or voice-activated, enabling the monitoring device 130 to serve as both an input and output device. Thus, settable items of the monitoring device 130 may be set, changed, or adjusted by using the buttons, touches to the screen of the monitoring device 130, or voices.

When the bronchoscope 115 captures images of the luminal network of the lung and the captured images do not need to be processed for visualization for human eyes, the monitoring device 130 may receive and display the captured images on the monitoring device 130 so that a clinician may confirm that the location of the catheter guide assembly 110 is in an intended place, particularly for use in confirmation of registration.

Although embodiments have been described in detail with reference to the accompanying drawings for the purpose of illustration and description, it is to be understood that the inventive processes and apparatus are not to be construed as limited. It will be apparent to those of ordinary skill in the art that various modifications to the foregoing embodiments may be made without departing from the scope of the disclosure.

What is claimed is:

1. A method for lung visualization using ultrasound (US) imaging, the method comprising:
    importing a first three-dimensional (3D) model of a luminal network of a lung;
    generating an electromagnetic (EM) field about the luminal network;
    sensing the EM field via an EM sensor;
    transmitting US waves via an US transducer;
    generating US images based on the US waves reflected from the luminal network, the EM sensor positioned at a distal portion of one of a first catheter and a second catheter and the US transducer positioned at a distal portion of the other one of the first and second catheters;
    processing the sensed EM field to measure a travelling distance of the EM sensor;
    scaling the travelling distance so that the scaled travelling distance is matched to a coordinate system of the first 3D model;
    replacing lower resolution portions of Computed Tomography (CT) image data from which the first 3D model was generated with the generated US images at a location of the US transducer based on the scaling of the travelling distance, yielding a modified CT image data;
    generating a second 3D model from the modified CT image data, wherein the second 3D model has a higher resolution than the first 3D model; and
    displaying the second 3D model.

2. The method according to claim 1, further comprising calculating a scale factor for the travelling distance between a coordinate system of the EM field and a coordinate system of the first 3D model.

3. The method according to claim 1, further comprising displaying a status related to the location of the EM sensor.

4. The method according to claim 3, wherein the status indicates whether the EM sensor is located at a not-in-target location, the target, or a location adjacent to healthy tissue.

5. The method according to claim 3, wherein the status indicates whether treatment of a target is complete.

6. The method according to claim 1, wherein generating the US images includes generating the US images at a resolution that is finer than a resolution of the first 3D model.

7. The system according to claim 1, wherein the EM sensor is located at the distal portion of the first catheter.

8. The method according to claim 1, further comprising recognizing a breathing pattern of a patient.

9. The method according to claim 8, further comprising identifying the location of the EM sensor based on the breathing pattern.

10. The method according to claim 1, wherein the generated US images are integrated near the location of the EM sensor in the first 3D model.

11. The method according to claim 1, further comprising identifying tissue density according to the reflected US waves.

12. The method according to claim 1, further comprising determining whether a treatment device is at a center of a target.

13. The method according to claim 1, further comprising determining a sufficiency of treatment in consideration of a density of a target according to the reflected US waves.

14. The method according to claim 1, further comprising detecting a size of a target.

15. The method according to claim 1, further comprising determining shrinkage of a target in real-time during and after a treatment of the target.

16. The method according to claim 1, further comprising determining an offset between the EM sensor and the US transducer.

17. The method according to claim 16, wherein a location of integration of the generated US images with the first 3D model is determined by the offset.

18. The method according to claim 1, wherein the US transducer is positioned distal of the EM sensor.

19. A method for lung visualization using ultrasound (US) imaging, the method comprising:

importing a first three-dimensional (3D) model of a luminal network of a lung;
generating an electromagnetic (EM) field about the luminal network;
sensing the EM field via an EM sensor;
transmitting US waves via an US transducer;
generating US images based on a reflection of the US waves from the luminal network, the EM sensor positioned at a distal portion of one of a first catheter or a second catheter and the US transducer positioned at a distal portion of the other one of the first or second catheters;
processing the sensed EM field and the reflected US waves to determine whether a new target is detected;
registering the new target to the first 3D model when it is determined that the new target is detected;
replacing lower resolution portions of Computed Tomography (CT) image data from which the the first 3D model was generated with the generated US images at a location of the US transducer based on a detection of the new target, yielding a modified CT image data;
generating a second 3D model from the the modified CT image data, wherein the second 3D model has a higher resolution than the first 3D model; and
displaying the second 3D model.

20. A method for lung visualization using ultrasound (US) imaging, the method comprising:

importing a first three-dimensional (3D) model of a luminal network of a lung;
generating an electromagnetic (EM) field about the luminal network;
sensing the EM field via an EM sensor;
transmitting US waves via an US transducer;
generating US images based on a reflection of the US waves from the luminal network, the EM sensor positioned at a distal portion of one of a first catheter or a second catheter and the US transducer positioned a predetermined distance from the EM sensor at a distal portion of the other one of the first or second catheters;
replacing lower resolution portions of Computed Tomography (CT) image data from which the first 3D model was generated with the generated US images at a location of the US transducer based on the predetermined distance, yielding a modified CT image data;
generating a second 3D model from the modified CT image data, wherein the second 3D model has a higher resolution than the first 3D model; and
displaying the second 3D model.

\* \* \* \* \*